United States Patent
Bell et al.

(10) Patent No.: US 12,360,125 B2
(45) Date of Patent: Jul. 15, 2025

(54) BIOSENSOR FOR COAGULATION TESTING

(71) Applicant: Zomedica Biotechnologies LLC, Ann Arbor, MI (US)

(72) Inventors: Florian Bell, Bend, OR (US); Bruce Murdock, Bend, OR (US)

(73) Assignee: Zomedica Biotechnologies LLC, Ann Arbor, MI (US)

( * ) Notice: Subject to any disclaimer, the term of this patent is extended or adjusted under 35 U.S.C. 154(b) by 1370 days.

(21) Appl. No.: 16/319,412

(22) PCT Filed: Jul. 25, 2017

(86) PCT No.: PCT/US2017/043732
§ 371 (c)(1),
(2) Date: Jan. 21, 2019

(87) PCT Pub. No.: WO2018/022620
PCT Pub. Date: Feb. 1, 2018

(65) Prior Publication Data
US 2019/0250176 A1 Aug. 15, 2019
US 2020/0256881 A9 Aug. 13, 2020

Related U.S. Application Data

(60) Provisional application No. 62/366,578, filed on Jul. 25, 2016.

(51) Int. Cl.
*G01N 33/86* (2006.01)
*B01L 3/00* (2006.01)
(Continued)

(52) U.S. Cl.
CPC ........ *G01N 33/86* (2013.01); *B01L 3/502715* (2013.01); *G01N 11/10* (2013.01);
(Continued)

(58) Field of Classification Search
None
See application file for complete search history.

(56) References Cited

U.S. PATENT DOCUMENTS

| 4,640,756 A | 2/1987 | Wang et al. |
| 5,798,452 A | 8/1998 | Martin et al. |

(Continued)

FOREIGN PATENT DOCUMENTS

| WO | WO 2014/143680 A | 9/2014 |
| WO | 2018022758 A1 | 2/2018 |

(Continued)

OTHER PUBLICATIONS

Voiculescu, I., et al., "Acoustic wave based MEMS devices for biosensing applications," 2012, Biosensors and Bioelectronics, 33(1): 1-9. (Year: 2012).*

(Continued)

*Primary Examiner* — Matthew D Krcha
(74) *Attorney, Agent, or Firm* — Standley Law Group LLP; Jeffrey S. Standley; Bryan P. Finneran

(57) ABSTRACT

Sensors employing bulk acoustic wave (BAW) resonators are used to assay characteristics of blood. The BAW sensors may be used to sense viscosity of a sample comprising blood to determine coagulation properties of the blood. The viscosity of the blood may be evaluated in the presence of agents that inhibit coagulation or that promote coagulation. The change in viscosity of the sample in the presence of such agents may provide information regarding whether the blood suffers from a coagulation disorder.

20 Claims, 12 Drawing Sheets

(51) Int. Cl.

| | | |
|---|---|---|
| | *G01N 11/10* | (2006.01) |
| | *G01N 11/16* | (2006.01) |
| | *G01N 15/06* | (2006.01) |
| | *G01N 29/02* | (2006.01) |
| | *G01N 29/036* | (2006.01) |
| | *G01N 29/22* | (2006.01) |
| | *G01N 30/96* | (2006.01) |
| | *G01N 33/49* | (2006.01) |
| | G01N 15/00 | (2006.01) |
| | G01N 15/01 | (2024.01) |

(52) U.S. Cl.
CPC ......... *G01N 11/16* (2013.01); *G01N 15/0637* (2013.01); *G01N 29/022* (2013.01); *G01N 29/036* (2013.01); *G01N 29/222* (2013.01); *G01N 30/96* (2013.01); *G01N 33/4905* (2013.01); *B01L 2300/023* (2013.01); *B01L 2300/0636* (2013.01); *B01L 2300/0816* (2013.01); *B01L 2300/0867* (2013.01); *B01L 2400/0436* (2013.01); *G01N 2015/0092* (2013.01); *G01N 15/01* (2024.01); *G01N 2203/0089* (2013.01); *G01N 2203/0092* (2013.01); *G01N 2291/02466* (2013.01); *G01N 2291/0255* (2013.01); *G01N 2291/0256* (2013.01); *G01N 2291/02818* (2013.01); *G01N 2291/0426* (2013.01); *G01N 2291/106* (2013.01)

(56) References Cited

U.S. PATENT DOCUMENTS

| | | | |
|---|---|---|---|
| 8,409,875 B2 | 4/2013 | Johal et al. | |
| 9,922,809 B2 | 3/2018 | McCarron et al. | |
| 2004/0150296 A1* | 8/2004 | Park | G01N 29/30 310/324 |
| 2007/0244520 A1* | 10/2007 | Ferren | A61B 5/4839 607/2 |
| 2009/0025459 A1* | 1/2009 | Zhang | A61B 5/0031 73/54.41 |
| 2012/0100636 A1 | 4/2012 | Johal et al. | |
| 2012/0195797 A1 | 8/2012 | Sparks et al. | |
| 2012/0297859 A1 | 11/2012 | Yu et al. | |
| 2017/0110300 A1 | 4/2017 | McCarron et al. | |

FOREIGN PATENT DOCUMENTS

| | | |
|---|---|---|
| WO | WO 2018/022620 A1 | 2/2018 |
| WO | WO 2018/022757 A | 2/2018 |
| WO | WO 2018/022778 A | 2/2018 |

OTHER PUBLICATIONS

U.S. Appl. No. 62/366,578, filed Jul. 25, 2016, Bell et al.
U.S. Appl. No. 62/368,261, filed Jul. 29, 2016, Edwards et al.
U.S. Appl. No. 62/370,788, filed Aug. 4, 2016, Bell et al.
PCT/US2017/043732, Jul. 25, 2017, Bell et al.
PCT/US2017/043958, Jul. 26, 2017, Bell et al.
PCT/US2017/043992, Jul. 26, 2017, Edwards et al.
International Patent Application No. PCT/US2017/043732, filed Jul. 25, 2017; International Search Report / Written Opinion issued Nov. 27, 2017; 11 pages.
International Patent Application No. PCT/US2017/043732, filed Jul. 25, 2017; International Preliminary Report on Patentability issued Feb. 7, 2019; 23 pages.
Kanazawa, K. Keiji, et al., "Frequency of a Quartz Microbalance in Contact with Liquid," 1985, *Analytical Chemistry*, 57(8):1770-71.
Lei et al., "Real-Time Electrical Impedimetric Monitoring of Blood Coagulation Process under Temperature and Hematocrit Variations Conducted in a Microfluidic Chip," Oct. 2013, *PLOS One*, 8(10): 7 pages.
Martin, Stephen J., et al., "Characterization of a Quartz Crystal Microbalance with Simultaneous Mass and Liquid Loading," 1991, *Analytical Chemistry*, 63(20):2272-81.
Martin et al., "Equivalent-Circuit Model for the Thickness-Shear Mode Resonator with a Viscoelastic Film near Film Resonance," Oct. 20, 1999, Microsensor Research and Development Department, Sandia National Laboratories; Albuquerque, New Mexico, 35 pages.
Martin, Stephen J., et al., "Equivalent-Circuit Model for the Thickness-Shear Mode Resonator with a Viscoelastic Film Near Film Resonance," 2000, *Analytical Chemistry*, 72(1):141-149.
Yang, C-L, et al., "Design and Evaluation of a Portable Optical-Based Biosensor for Testing Whole Blood Prothrombin Time," *Talanta*, vol. 116, Nov. 15, 2013, pp. 704-711.

* cited by examiner

BIOSENSOR FOR COAGULATION TESTING

RELATED APPLICATIONS

This application is the $371 U.S. National Stage of International Application No. PCT/US2017/043732, filed 25 Jul. 2017, which claims priority to U.S. Provisional Application Ser. No. 62/366,578, filed on 25 Jul. 2016, the disclosures of which are incorporated by reference here in their entireties.

FIELD

The present disclosure relates to bulk acoustic wave (BAW) resonators and their use as biosensors. In particular, the present disclosure relates to bulk acoustic wave resonators adapted for measurement of characteristics of blood samples such as viscosity of the blood samples.

BACKGROUND

Coagulation of blood is a natural mechanism that can restrict blood flow at or near a site of damage to body tissue. Coagulation is a multi-step process that includes a cascade of reactions generally referred to as a pathway. The pathway includes a balanced series of reactions and transformations of biochemicals that are activated by secondary processes. Ultimately, the pathway leads to the formation of fibrin, a polymerized protein that binds to blood platelets, inhibiting blood flow and leading to the formation of a plug or clot when the fibrin cross-links.

A number of coagulation disorders exist, including deficient clotting and excessive clotting. In many cases, deficient clotting may be corrected by administration of a clotting factor or other suitable agent. In many cases, excessive clotting may be treated by administration of a blood thinner, an anti-clotting agent, or other suitable agent. Identification of clotting disorders and determining appropriate dosages of suitable agents to treat the disorder may be important for patients having a coagulation disorder.

It may be desirable to perform testing for blood coagulation at a point-of-care setting, such as a physician's office or a hospital. Test strips for the purpose of coagulation testing are commercially available and generally test a single stage in the coagulation pathway. However, systems and methods for more convenient testing, including conveniently testing multiple stages of the coagulation pathway, are desired.

SUMMARY

The present disclosure describes the use of sensors employing bulk acoustic wave (BAW) resonators to assay characteristics of blood. In particular, the BAW sensors may be used to sense viscosity of a sample comprising blood to determine coagulation properties of the blood. The viscosity of the blood may be evaluated in the presence of agents that inhibit coagulation or that promote coagulation. The change in viscosity of the sample in the presence of such agents may provide information regarding whether the blood suffers from a coagulation disorder. Appropriate dosages of medications to treat a coagulation disorder may be determined based on the sensed viscosity.

In some aspects, one or more BAW sensors are used to quantify or determine the presence of various factors in the blood sample, which may provide additional information regarding the ability of the blood to coagulate. When used in combination with viscosity sensing, enhanced information regarding coagulation of the blood may be obtained. Accordingly, substantial information regarding blood coagulation may be obtained from a single instrument.

In a first aspect, a method for measuring one or more characteristics of blood is described herein. The method includes driving a first bulk acoustic wave (BAW) resonator having a sensing surface into oscillating motion; flowing a sample comprising the blood across the sensing surface of the first oscillating BAW resonator; detecting a resonance characteristic of the first BAW resonator while the sample is in contact with the sensing surface; and converting the detected resonance characteristic to a value indicating viscosity of the sample. The viscosity may provide insight into the coagulation status of the blood in the sample.

The method may further comprise driving a second bulk acoustic wave (BAW) resonator having a sensing surface into oscillating motion; flowing the sample comprising the blood across the sensing surface of the second oscillating BAW resonator; detecting a resonance characteristic of the second BAW resonator while the sample is in contact with the sensing surface; and converting the detected resonance characteristic to a value indicating viscosity of the sample. The value indicating viscosity at the first BAW resonator may be compared to the value indicating viscosity at the second BAW resonator to provide further insight into the coagulation status of the blood. The sample may flow across the second resonator after flowing over the first resonator so that the coagulation status of the blood may be monitored over time. The sample may be agitated, which may promote coagulation of blood in the sample, prior to flowing over the first or second resonator. The sample may be mixed with one or more coagulation-modifying agents to determine the effect of the agents on coagulation of the blood.

The method may further comprise driving a third bulk acoustic wave (BAW) resonator having a sensing surface into oscillating motion, wherein the sensing surface comprises a biomolecule that specifically binds to a molecule in blood; flowing the sample comprising the blood across the sensing surface of the second oscillating BAW resonator; detecting a resonance characteristic of the second BAW resonator while the sample is in contact with the sensing surface; and converting the detected resonance characteristic to a concentration of the molecule in the sample. Thus, additional information regarding the concentration of molecules in the blood may be used in combination with coagulation status to provide enhanced information that may be beneficial for determining a disease state of the blood.

In a second aspect, a bulk acoustic wave (BAW) sensing device for determining characteristics of blood is described herein. The device includes a viscosity sensor comprising a first array of BAW resonators, each having a sensing surface; a biosensor comprising a second array of BAW resonators, each having a sensing surface, wherein the sensing surface of at least one BAW resonator comprises a biomolecule that specifically binds a molecule in blood; a sample port for introducing a sample comprising blood; and a flow path from the sample path to the first array of BAW resonators and to the second array of BAW resonators.

The flow path may have a branch region separating the flow path into a first branch and a second branch. The BAW resonators of the first array are in the flow path of the first branch, and the BAW resonators of the second array are in the flow path of the second branch. The device may include an agitator element in the flow path of the second branch. The agitator element is configured to agitate the sample to cause the blood in the sample to coagulate.

In a third aspect, a bulk acoustic wave (BAW) sensing device is described herein. The device includes a viscosity sensor comprising a first array of BAW resonators and a second array of BAW resonators; a sample port for introducing a sample comprising blood; a flow path from the sample path to the first array of BAW resonators and to the second array of BAW resonators, wherein the flow path comprises a branch region separating the flow path into a first branch and a second branch, wherein the BAW resonators of the first array are in the flow path of the first branch, and wherein the BAW resonators of the second array are in the flow path of the second branch; and an agitator element in the second branch of the flow path, wherein the agitator element is configured to agitate the sample to cause the blood in the sample to coagulate.

One or more aspects of devices, methods and systems described herein may have one or more advantages over current devices, methods and systems for testing coagulation of blood. In particular, testing blood coagulation with a BAW sensor has several advantages. For example, BAW sensors are sensitive to small changes in viscosity, making them ideal sensors for detecting changes in viscosity due to coagulation of blood. In addition, BAW sensors are inherently small, so very small samples of blood may be used. Furthermore, BAW biosensors are inherently fast and can react to changes in viscosity quickly. These and other advantages will be apparent to those of skill in the art upon reading the disclosure presented herein.

Figure 1:
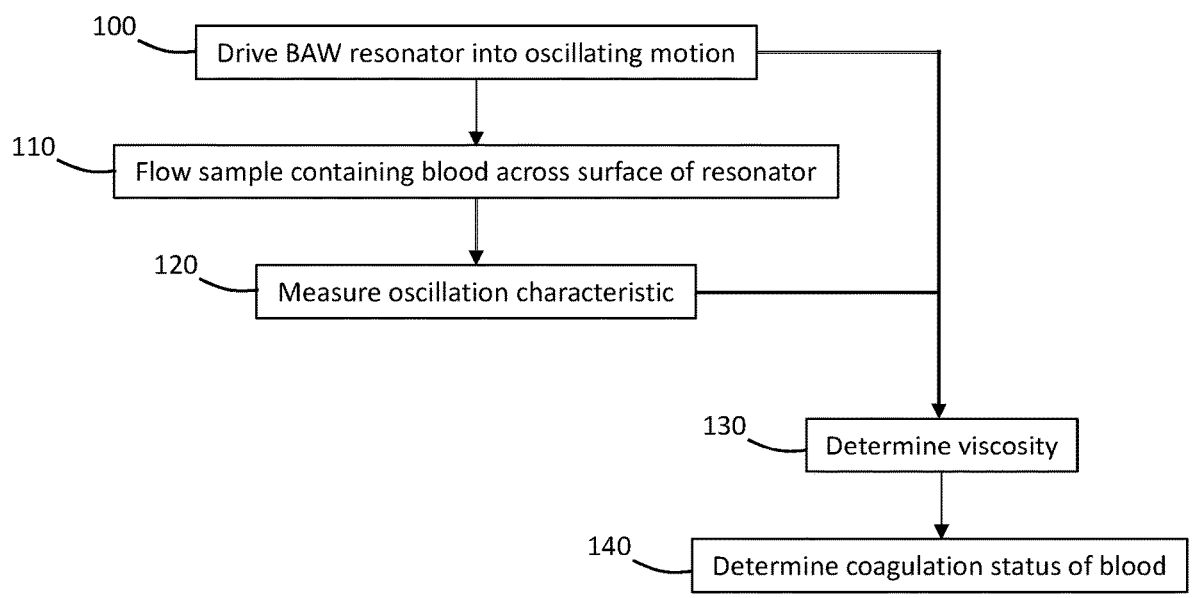
FIGS. 1-6 are flow diagrams of methods according to various embodiments described herein.

Like numbers used in the figures refer to like components, steps and the like. However, it will be understood that the use of a number to refer to a component in a given figure is not intended to limit the component in another figure labeled with the same number. In addition, the use of different numbers to refer to components in different figures is not intended to indicate that the different numbered components cannot be the same or similar to other numbered components. The figures are presented for purposes of illustration and not limitation. Schematic drawings presented in the figures are not necessarily to scale.

DETAILED DESCRIPTION

In the following detailed description, several specific embodiments of compounds, compositions, products and methods are disclosed. It is to be understood that other embodiments are contemplated and may be made without departing from the scope or spirit of the present disclosure. The following detailed description, therefore, is not to be taken in a limiting sense.

The present disclosure relates to bulk acoustic wave (BAW) resonators and their use as biosensors. In particular, the present disclosure relates to bulk acoustic wave resonators adapted for measurement of characteristics, such as viscosity, of blood samples. According to embodiments, BAW biosensors may be configured for detection of viscosity and density levels in mammalian blood, indicative of stages of disease or of stages of coagulation. By provision of various agents that may promote, slow, or advance the properties of the blood coagulation during testing, the sensor may be tuned to be sensitive to changes in viscosity levels indicative of the degree of disease or of coagulation at various stages of the coagulation-relevant pathways.

In various embodiments described herein, information regarding the fluidic properties of blood are combined with detection or quantification of one or more molecules present in the blood. To provide a more complete set of information regarding the status of the blood, which may be helpful to physicians in determining an appropriate treatment option for a patient with a blood disorder.

A sample containing the blood (e.g., whole blood, serum, or plasma) is caused to flow across the surface of a BAW resonator that has been driven into oscillating motion. An oscillation characteristic, such as frequency, phase, amplitude, Q-factor, or the like, as a result of the sample flowing across the resonator is measured. A viscosity of the sample may be determined based on the oscillation characteristic. It will be understood that an oscillation characteristic will change based on the fluid properties of the sample and that a change in oscillation characteristic may not be entirely a change in viscosity, but may also comprise a change in density component. For purposes of the present disclosure, changes in specific density and viscosity are collectively referred to as changes in viscosity. The status of the blood, particularly the coagulation state of the blood, may be derived from the determined viscosity.

The sample may be agitated prior to or while the sample is flowing across the resonator. The agitation may cause the blood to initiate a clotting reaction. The change in viscosity of the sample may be monitored over time by flowing the previously agitated blood over another BAW resonator downstream of the first sensor. In addition or alternatively, the sample comprising blood may flow across a first BAW resonator without being agitated and may flow across a second sensor after agitation. Changes in viscosity of blood that has been agitated relative to blood that has not been agitated may be determined.

The sample containing the blood may be mixed with one or more agents know to promote or inhibit coagulation or clotting of blood and the effect of the of the agent on the viscosity of the blood, with or without agitation, may be determined.

In addition, the sample containing the blood may be caused to flow across the surface of a BAW resonator having a molecule on the surface configured to bind to one or more molecule or component of blood. Changes in oscillation due to binding of the molecules as the sample crosses the resonator may be measured. The changes in oscillation may be correlated to the presence or concentration of the molecule or component in the sample.

By combining changes in viscosity, with or without one or more clot promoting or inhibiting agents, with the presence or concentration of one or more molecule of component of blood, a more complete set of information regarding the status of the blood may be provided.

Referring now to FIG. 1, an overview of a method is shown. The method includes driving a BAW resonator into an oscillating motion (100) and causing a sample containing blood to flow across the surface of the resonator (110). An oscillation characteristic of the resonator, such as one or more of frequency, phase, amplitude, Q-factor, and the like, is measured (120) when the sample is in contact with the resonator. Viscosity of the sample may be determined (130) based on the measured oscillation characteristic. Viscosity can be determined by calibration the response of the resonator to solutions of known viscosity and fitting the measured oscillation characteristic (e.g., in step 120) to the calibration curve. The viscosity may be calculated based on the oscillation characteristic in any other suitable manner. The coagulation status of the blood may be determined (140) based on the determined viscosity. Generally, higher viscosity will be indicating of greater coagulation and lower viscosity will be indicative of less coagulation.

The method depicted in FIG. 1 may be a part of other methods described herein.

Figure 2:
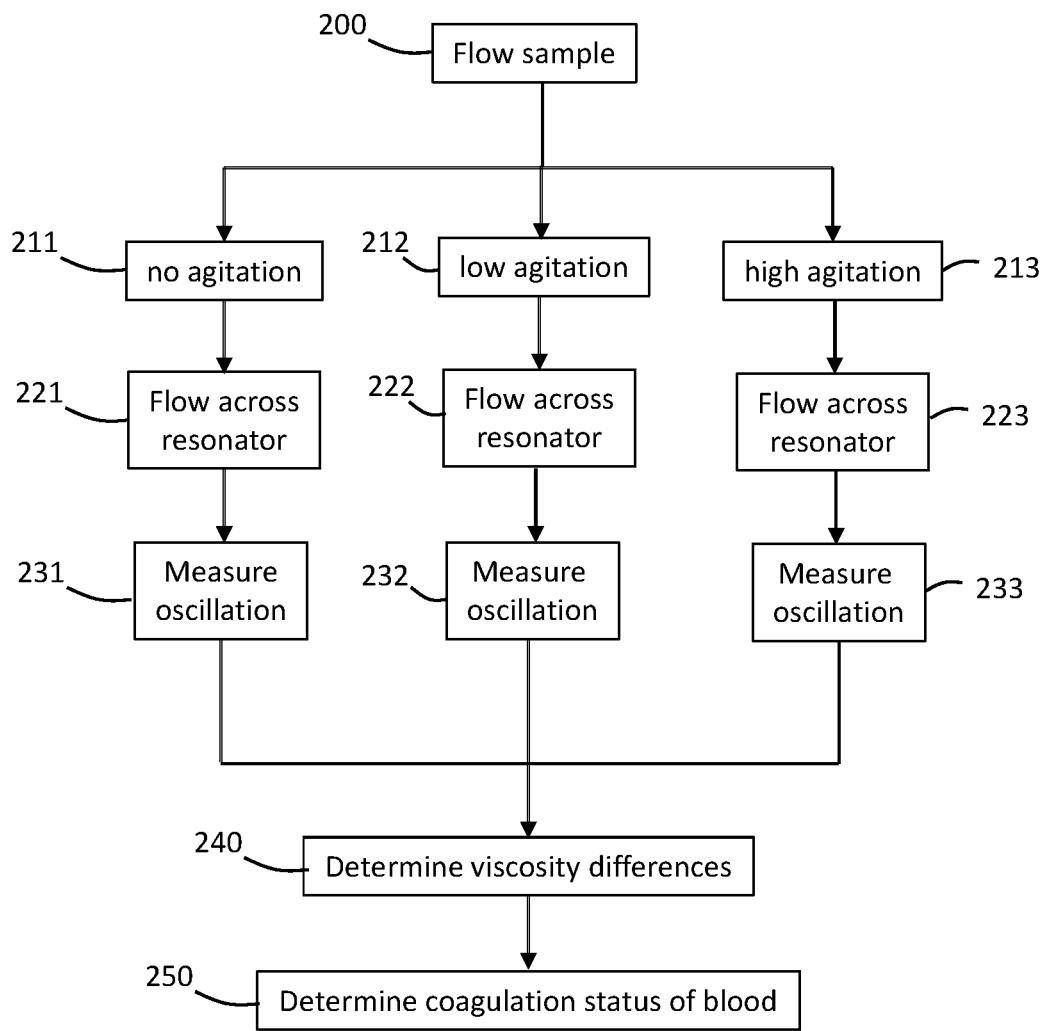

Referring now to FIG. 2, a method that includes agitation of the sample containing the blood is shown. The method includes flowing the sample through one or more flow paths (200). The sample may flow across a first flow path in which there is no agitation (211), low levels of agitation (212), high levels of agitation (213) or any intermediary levels of agitation. The agitation may facilitate coagulation or clotting of the blood. The blood may be agitated in any suitable manner. For example, agitation may be active or passive. Examples of active agitation include acoustic or ultrasonic, dielectrophoretic, electrokinetic time-pulse, pressure perturbation, electro-hydrodynamic, magnetic or thermal agitation. Examples of passive agitation include placement of one or more features or valves, such as a Venturi valve, in the flow path to cause turbulent flow. Preferably, the agitation is passive.

Each portion of the sample that has been agitated to a differing degree may be caused to flow across a resonator (221, 222, 223) and an oscillation characteristic may be measured (231, 232, 233). The viscosities based on the differing levels of agitation may be calculated or compared (240), and the coagulation of the status may be determined (250) based on the viscosities.

Figure 3:
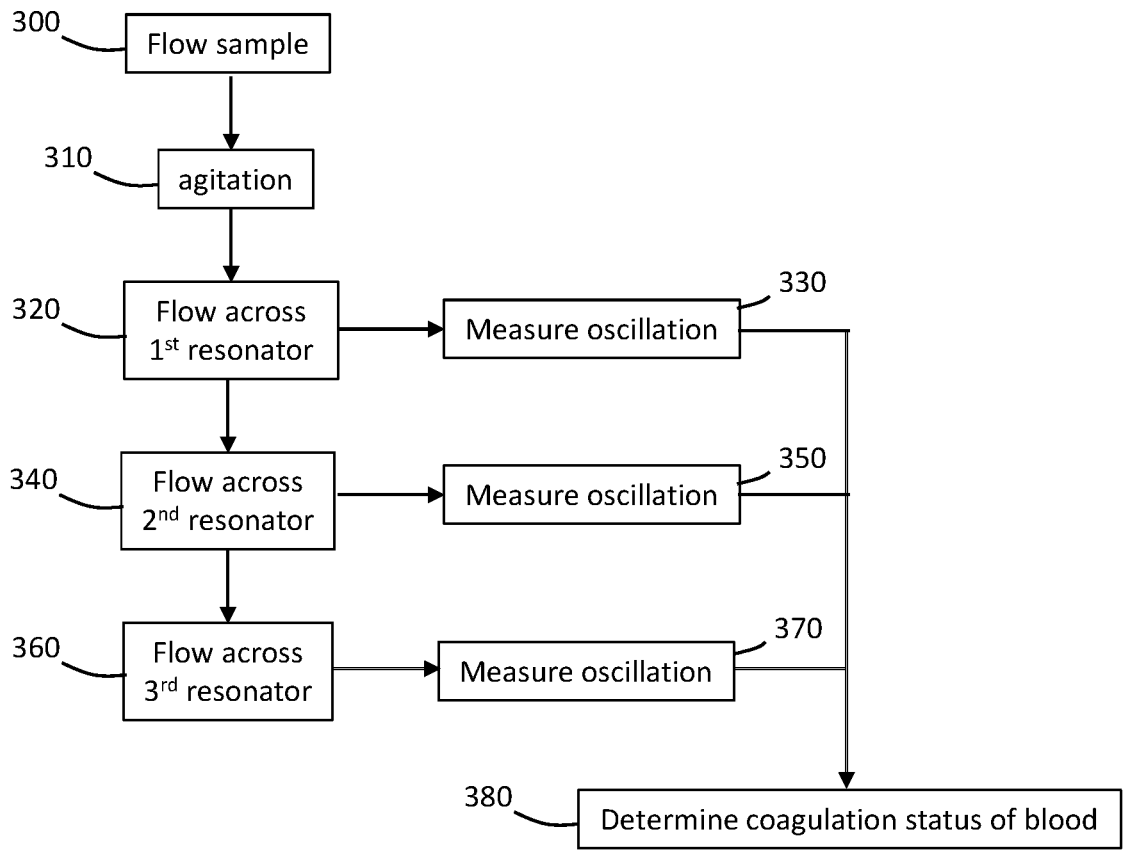

In addition to, or as alternative to, the method depicted in FIG. 2, the method in FIG. 3 may be performed. Like the method depicted in FIG. 2, the method depicted in FIG. 3 includes agitating the sample and determining the coagulation status of the blood in the sample following the agitation. The method depicted in FIG. 3 includes flowing the sample containing the blood through a flow path (300), such as a flow path discussed regarding FIG. 2, and agitating the sample (310). The agitated sample may be caused to flow across a first resonator (320) and an oscillation characteristic is measured (330). The sample then flows across a second resonator (340) after a period of time and an oscillation characteristic is measured (350). The sample then optionally flows across a third resonator (360) after a period of time and an oscillation characteristic is measured (370). The coagulation status of the blood in the sample may be determined based on the change of oscillation characteristics or viscosity over time (380).

Figure 4:
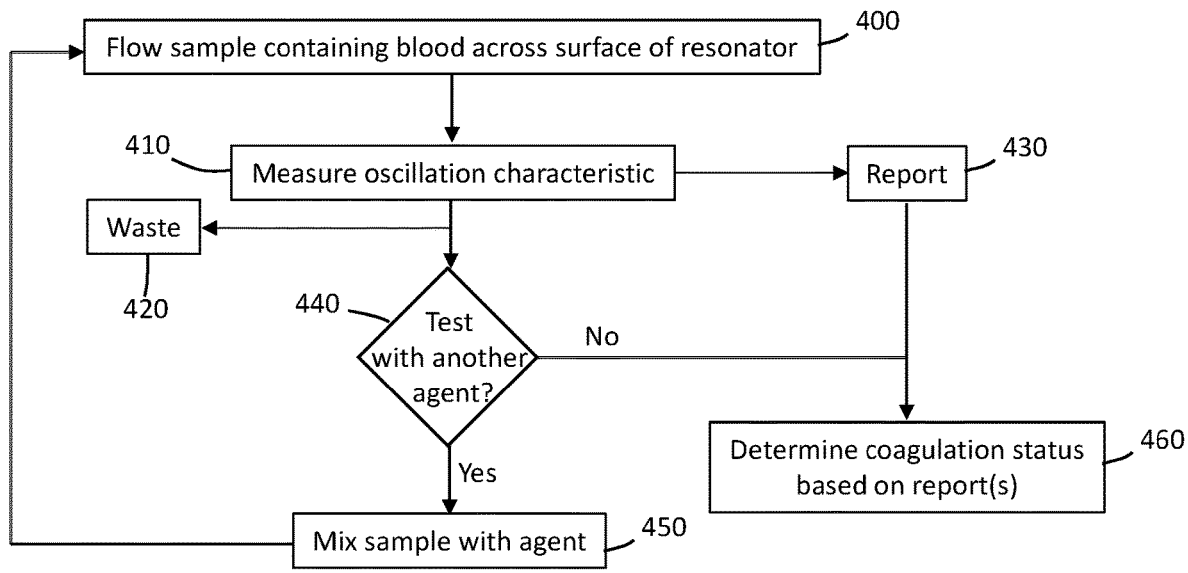

Referring now to FIG. 4, a method showing mixing of the sample with one or more agents and determining coagulation status based on sensor response in the presence or absence of the agents is shown. The method may optionally include flowing the sample with no added agent across the surface of a resonator (400) or resonators; e.g., as depicted in FIGS. 1-3, and an oscillation characteristic may be measured (410). The results of the measured oscillation characteristic may be reported (430), which may include storing the results in memory for later recall. The sample may then be directed for storage in waste (420). If additional agents are to be tested (440), one or more additional agents may be mixed with the sample (450) and the sample with mixed agents may flow across a surface of the resonator (400), oscillation characteristics measured (410), and results reported (430). The sample with mixed agents may be directed for storage in waste (420). If the sample with mixed agents flows across the resonator that was previously used, the sensor and flow path may be rinsed with buffer prior to flowing the sample with mixed agents through the flow path or across the sensor. Alternatively, the sample with mixed agents may be flowed across a different sensor. The process may be repeated until all agents or combinations of agents are combined with sample. When there are no additional agents or combination of agents to be mixed with the sample for testing, the coagulation status of the blood in the sample may be determined (460) based on the reports.

While the process depicted in FIG. 4 is depicted as taking place in series, it will be understood that parallel processing may be employed.

Any suitable agent or combination of agents may be mixed with the sample to evaluate the coagulation status of the blood. For example, the sample containing the blood may be mixed with a clotting rate enhancing agent that activates the contact (or intrinsic) pathway, activates a tissue factor (or extrinsic) pathway, or activates both pathways. Examples of contact pathway activators include kaolin, celite, silica, ellagic acid, phospholipids, etc. Examples of tissue factor pathway activators include thromboplastin (factor III). Tissue factor pathway activators tend to cause more rapid coagulation of blood than contact pathway activators.

The sample containing the blood may be mixed with an anticoagulant, or "blood thinner." Such agents include heparin and warfarin. The concentrations of anticoagulants may be varied and viscosities detected at the various BAW sensors may be used to derive a dosage that may be appropriate for a patient based on the coagulation status determined using the methods, devices and systems described herein.

Normally, blood clotting is a beneficial reaction in the body when plug formation is desired to prevent blood loss at a tissue damage site. However, various conditions may lead to excessive or unbalanced clot formation that can result in lack of blood flow to or from otherwise healthy areas of tissue or organs, leading to damage of the otherwise healthy areas. Thus, it may be desirable to control unbalanced coagulation through the use of blood thinners or other medications. One difficulty with the administration of blood thinners is the accurate estimation of the amount of thinning agent needed to obtain a therapeutic benefit without over-administration. Accordingly, the methods, devices and systems described herein may allow for appropriate dosage determination.

In some examples, it may be beneficial to mix the sample with a sufficiently high concentration of a clotting inhibitor, such as warfarin or heparin, to ensure that clotting does not occur during testing. In some example, the sample mixed with a high concentration of a clotting inhibitor may serve as a control against which coagulation may be compared. For example, coagulation in a blood sample containing no clotting inhibitor may be compared to coagulation containing a high concentration of clotting inhibitor (and thus no or little coagulation would be expected. Accordingly, a clotting inhibitor may be used in methods that may not be associated with determination of dosing.

The sample containing the blood may be mixed with one or more platelet activator to detect platelet dysfunction. If viscosity increases in the presence of a platelet activator, the platelets may be determined to be functioning normally. However, if viscosity does not change to a sufficient degree or in an expected amount of time, the blood may suffer from platelet dysfunction. Examples of platelet activators that may be used include collagen, adenosine diphosphate (ADP), epinephrine, and arachidonic acid.

The sample containing the blood may be mixed with fibrinogen or a fibrinolysis inhibiting agent. Fibrinolysis inhibiting agents include tranexamic acid, epsilon amino caproic acid, aprotinin, plasminogen activator inhibitor 1, plasminogen activator inhibitor 2, $\alpha_2$-antiplasmin, and $\alpha_2$-macroglobulin, and the like. If viscosity increases in the presence of fibrinogen, the blood may suffer from weak fibrin polymerization. The sample containing blood may be mixed with fibrinogen and a platelet inhibitor to evaluate the effect of fibrin or fibrinogen on coagulation in the absence of (or reduced) effect from platelets.

The agents discussed above are only examples of those that may be used with the devices, systems and methods described herein. It will be understood that other agents may be employed.

It will also be understood that the processes depicted in FIGS. 1-4 may be combined in any suitable manner so that a wealth of information regarding coagulation status of the blood may be obtained. For example, the sample may be is mixed with one or more agents that may affect coagulation or clotting of the blood in the sample. The mixed samples may follow one or more flow path configured to agitate fluid flowing through the path a predetermined degree. The BAW sensors may detect the viscosity of the mixed samples subjected to agitation, no agitation, or differing levels of agitation, and the differences in the viscosities may be determined and compared to evaluate the coagulation status of the blood. The mixed samples may be flowed across further downstream sensors to determine the change in viscosity over time to evaluate coagulation status of the blood.

Figure 5:
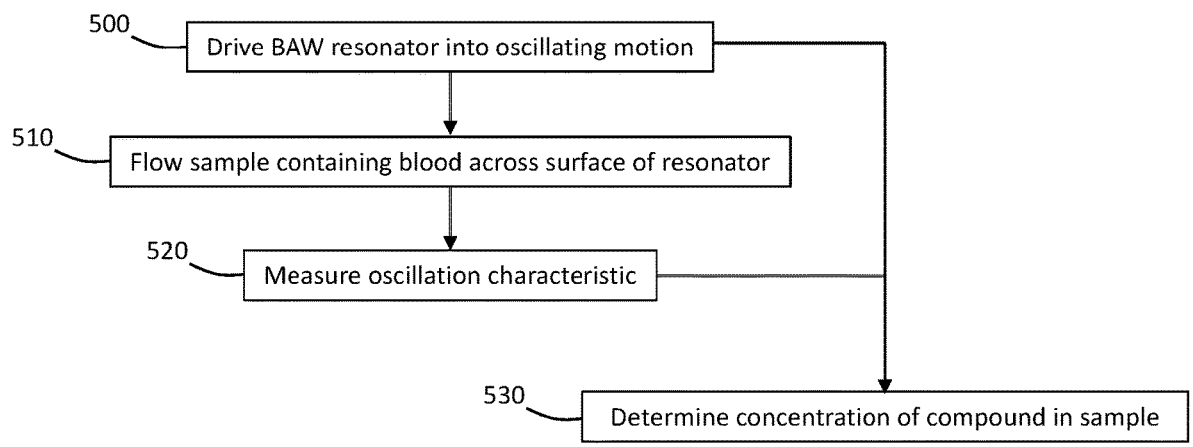

In addition, the sample containing the blood may be caused to flow across the surface of a BAW resonator having a molecule on the surface configured to specifically bind to one or more molecule or component of blood to determine the presence or concentration of the molecule or component in the sample. For example and with reference to FIG. 5, a method includes driving a BAW resonator into an oscillating motion (500). A sample containing blood is then caused to flow across the surface of the resonator (510), which has a molecule on the surface that selectively binds a molecule of component of blood. An oscillation characteristic is measured when the sample is in contact with the resonator (520). The presence or concentration of the molecules or components of blood in the sample are determined based on changes in oscillation due to binding of the molecule or component of blood in the sample to the surface of the resonator (530).

The surface of the resonator may be functionalized with any suitable molecule that specifically binds to a component or molecule in blood. For example, the surface may be functionalized with an antibody directed to Factor I (fibrinogen), Factor II (prothrombin), Factor III (tissue factor), Factor V (proaccelerin), Factor VII (proconvertin), Factor VIII (antihemophilic factor A), Factor IX (antihemophilic factor B or Christmas factor), Factor X (Stuart-Prower factor), Factor XI (plasma thromboplastin antecedent), Factor XII (Hageman factor), Factor XII (fibrin-stabilizing factor), von Willebrand factor, prekalikrein, high-molecular weight kininogen, fibronecting, antithrombin III, heparin cofactor II, protein C, protein S, protein Z, protein Z-related protease inhibitor, plasminogen, alpha 2-antiplasmin, tissue plasminogen activator, urokinase, plasminogen activator inhibitor-1, plasminogen activator inhibitor-2, cancer procoagulant, or the like. The role that these factors play in blood coagulation or clotting are well known. One of skill in the art will appreciate the implications of the presence and concentration of these agents in the blood of the sample as they relate to clotting or coagulation.

Figure 6:
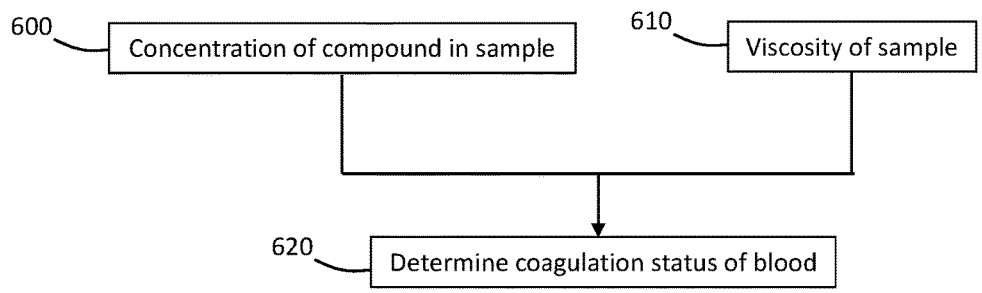

Referring now to FIG. 6, a method is shown where information regarding the concentration of a molecule or component of blood (600), such as discussed above regarding FIG. 5, is combined with information regarding the viscosity of the sample (610), which may be in the presence or absence of an agent, such as discussed above regarding FIGS. 1-4, to determine the coagulation status of blood in the sample (620).

Preferably, all the information discussed above may be obtained using a single system; particularly a sensor device and a reader. The BAW sensors may be present in a sensor device that may be placed in the reader to analyze coagulation of the blood. The sensor device may include a sample port into which a sample comprising blood may be placed. The sensor device may include a flow path from the sample port across the surface of the BAW sensors and appropriate valves or mixers and agitators.

The blood may be agitated as it flows from the sample port to the sensor. The agitation may facilitate coagulation or clotting of the blood. The sensor device may include alternate flow paths that allow for the sample comprising the blood to be agitated in one flow path and allow the blood to flow to the sensor without agitation in another flow path. The sensor device may include flow paths that subject the sample comprising blood to different intensities of agitation. The BAW sensors may detect the viscosity of the samples subjected to agitation, no agitation, or differing levels of agitation, and the differences in the viscosities may be determined and compared to evaluate the coagulation status of the blood.

The flow path or paths may continue across other BAW sensors so that changes in viscosity of the sample over time may be monitored. For example, the viscosity at a first BAW sensor may be compared to the viscosity at a second BAW sensor downstream of the first BAW sensor to determine the difference in viscosity over time (the time between the sample reaching the first sensor that the sample reaching the second sensor). The change in viscosity over time may be correlated to coagulation status of the blood.

In general, increased viscosity, which may correlate to, for example, decreased resonance frequency of the BAW resonator, may be correlated to increased coagulation.

The sample may be mixed with one or more agents that may affect coagulation of clotting of the blood in the sample. The mixed samples may follow one or more flow path configured to agitate fluid flowing through the path a predetermined degree. The BAW sensors may detect the viscosity of the mixed samples subjected to agitation, no agitation, or differing levels of agitation, and the differences in the viscosities may be determined and compared to evaluate the coagulation status of the blood. The mixed samples may be flowed across further downstream sensors to determine the change in viscosity over time to evaluate coagulation status of the blood.

Non-limiting examples of sensor devices and readers, or portions or components thereof, that may be employed to carry out the methods described above are discussed below regarding FIGS. 7-15B.

Figure 7:
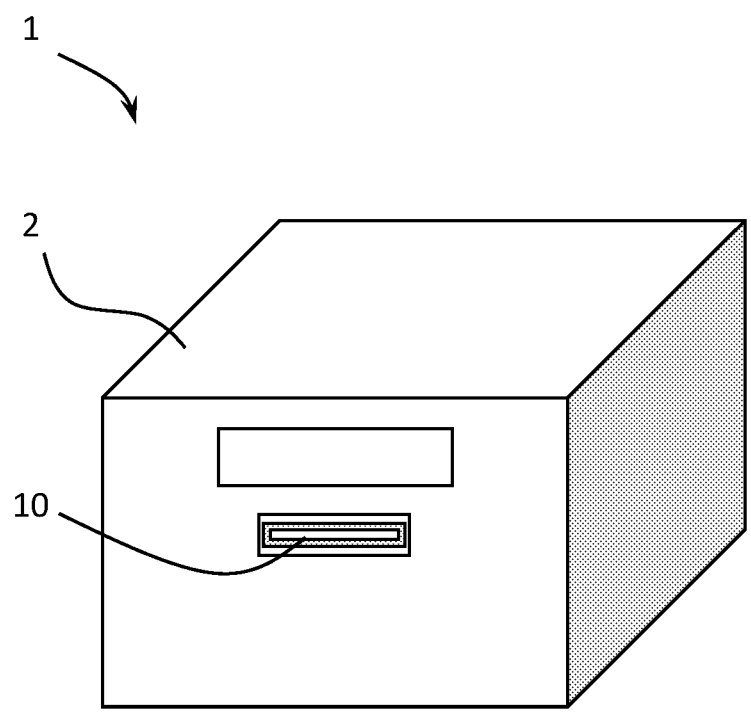
FIG. 7 is a schematic perspective view of an embodiment of a BAW sensing device and a reader.

Referring now to FIG. 7, an example of a system 1 that includes a sensor device 10 and a reader 2 is shown. The sensor device 10 is received by the reader 2 such that the sensor device is fluidly and electrically coupled to components of the reader 2. The reader 2 may provide solutions used in sample handling in the sensor device 10, and may be used to read and optionally interpret the results from the BAW sensor in the device 10. The sensor device 10 may embody integrated components necessary to convert a BAW resonator, or array of BAW resonators, into a biosensor. This allows for a collection of the tools integrated into a single device that can be tailored for the detection of viscosity of a sample containing blood and one or more molecules or components of blood in the sample.

Figure 8:
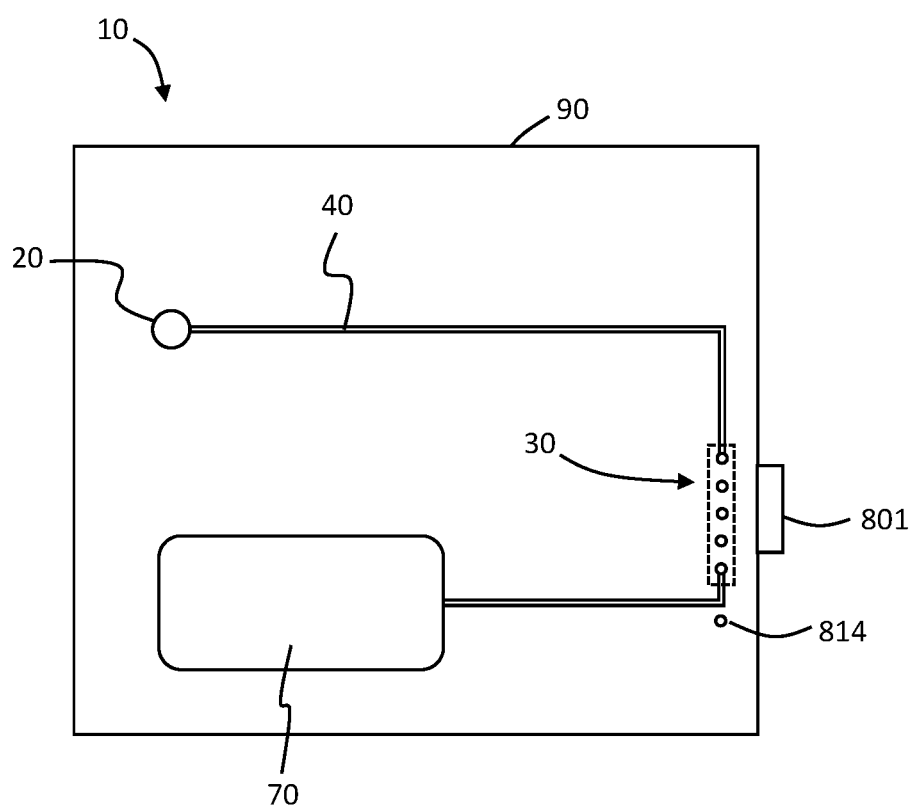
FIG. 8 is a schematic plan view of an embodiment of a BAW sensing device illustrating some components of the device.

Referring now to FIG. 8, an example of a BAW sensor device 10 is shown. The sensor device 10 includes a sample port 20 into which a blood sample (e.g., whole blood, serum, or plasma) may be applied. The blood sample may be introduced into the port as-is without pre-treatment, or may be pre-treated, for example by filtering, centrifuging, or adding one or more agents to the blood. In some embodiments, the blood sample is whole blood. In another embodiment, the blood sample is serum. A small sample volume, such as from about 10 µL to about 200 µL, or from about 20 µL to about 150 µL, or from about 50 µL to about 120 µL, or any other suitable volume may be used.

One or more agents, such as viscosity-altering agents, coagulation agents, coagulation inhibitors, buffers, etc., can be applied to the sample. The sample is then driven through a flow path 40 extending from the sample port 20 across one or more BAW sensors to a waste reservoir 70. As the sample flows across the one or more BAW sensors 30, viscosity, concentration of molecules, or other aspects may be measured. The device 10 may include isolated environmental BAW reference 814.

The BAW sensor device 10 may be constructed to provide sample handling, conditioning, and delivery to the BAW sensors within the device. The fluid flow path 40 and the BAW sensor 30 may be housed in a housing 90, such as a cartridge. An example cartridge is disclosed in more detail in U.S. Provisional Patent Application No. 62/368,261, filed on 29 Jul. 2016, which application is incorporated here by reference in its entirety to the extent that it does not conflict with the present disclosure.

The sensor device 10 may further include various fluid ports, fluid reservoirs, and/or fluid channels for providing agents and sample-handling fluids. The sensor device 10 may either be provided with internal liquid-handling capabilities, such as storage (e.g., one or more fluid reservoirs), valves, and pumps for such agents and sample-handling fluids, or may be constructed to connect to external liquid-handling systems. For example, the BAW sensor device 10 may be constructed to be received in a reader 2, and may include various features for interfacing with the reader 2, such as one or more electrical interconnect 801. For example, fluid ports on the BAW sensor device 10 may interface with valves, pumps, or other fluidic interfaces for pneumatic or liquid-based fluid transfer systems on the reader. Other embodiments of the cartridge 10 may also include additional valves and fluid flow management features, such as pumps. The BAW sensor device 10 may also include mechanical registrations to position the cartridge within the reader 2, and interfaces for electrical current (e.g., direct current or alternating current) and power and digital communication signals, magnetic interfaces, thermal interfaces, and/or optical interfaces.

Figure 9:
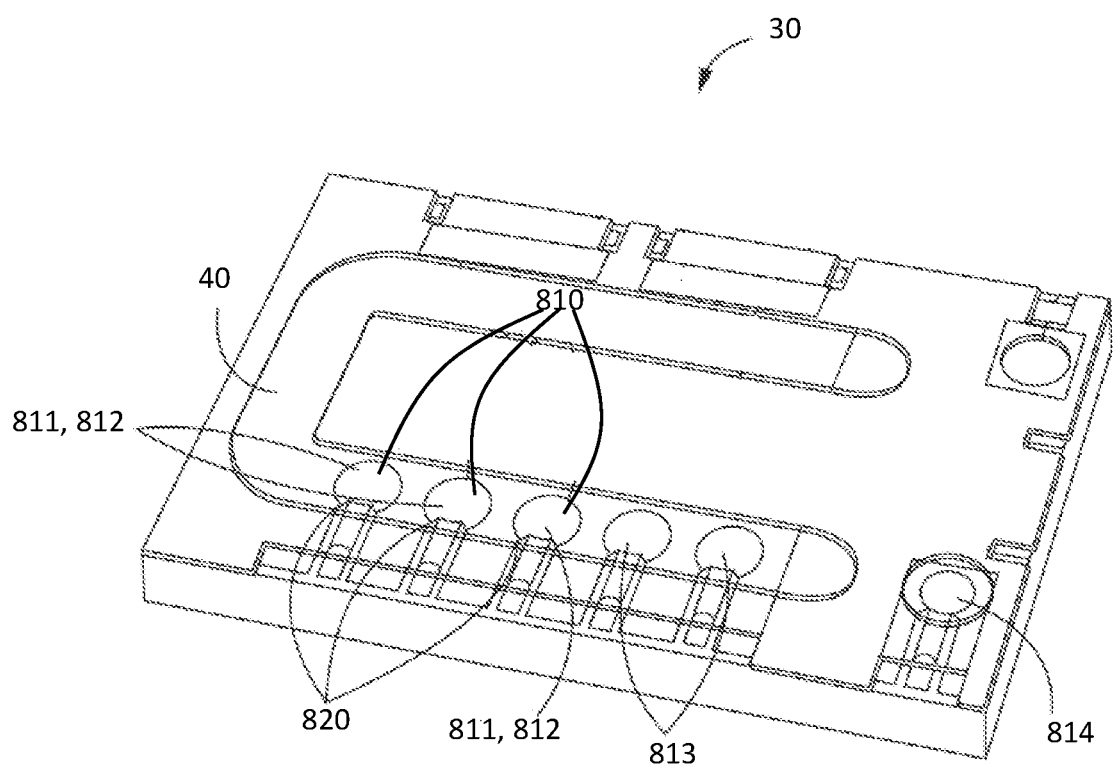
FIG. 9 is a schematic perspective view of an embodiment of a sensor portion of a BAW sensing device.

Referring now to FIG. 9, the BAW sensor 30 may comprise at least one BAW resonator 810 having a sensing surface 811. The BAW sensor 30 may include an array 820 of BAW resonators 810. The BAW resonators 810 may be disposed along the fluid flow path 40 such that fluid (e.g., a sample) flowing in the fluid flow path 40 contacts the sensing surfaces 811 of the various BAW resonators 810. The BAW resonators 810 can be arranged in an array that includes multiple BAW resonators 810 of either the same or different types.

One or more of the resonators 810, such as the resonators of array 820, may serve as a viscosity sensor in which the BAW resonators 810 are adapted for measuring the viscosity of a sample. The BAW sensor 30 may also include other types of BAW resonators providing different sensing capabilities, such as BAW resonators with one or more biomolecules attached to their sensing surfaces, which biomolecules may specifically bind to one or more molecule or component of blood. In the example depicted in FIG. 9, the BAW sensor 30 includes six BAW resonators that are divided into three viscosity sensors 830, two BAW resonators 813 having biomolecules bound to their surface for specific interaction of molecules or components of blood, and an isolated environmental BAW reference 814. However, the sensor is not limited to six BAW resonators, and could include any number, such as from one to fifty resonators.

Figure 10A:
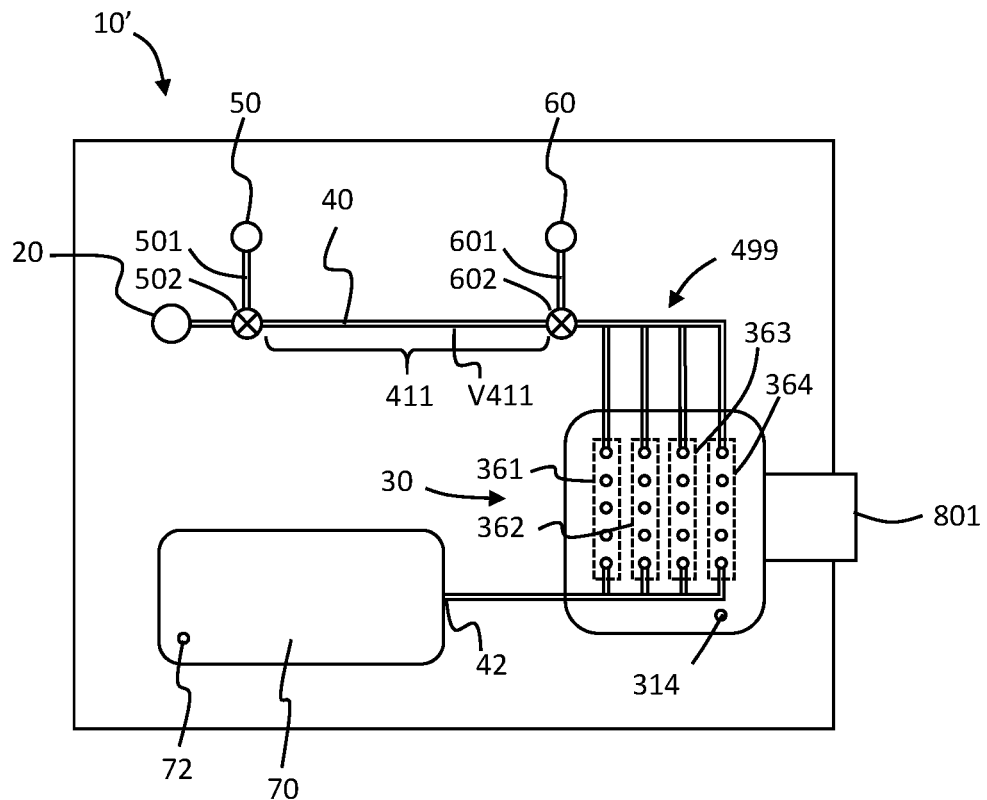
FIG. 10A is a schematic plan view of an embodiment of a BAW sensing device illustrating some components of the device.
Figure 10B:
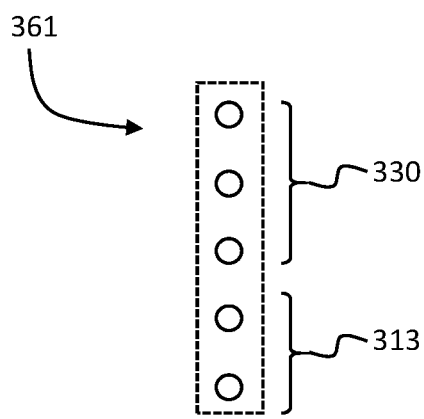
FIG. 10B is a schematic plan view of an embodiment of an array of resonators of BAW sensing device.

Another example of a BAW sensing device 10' is depicted in FIGS. 10A-B. The device 10 includes a sensor 30 having a plurality of arrays 361, 362, 363, 364 of resonators and an isolated environmental BAW reference 814. One or more of the arrays 361, 362, 363, 364 may include resonators for sensing viscosity and resonators for sensing the presence or concentration of molecules or components of blood in the sample. The number of arrays and resonators in the arrays may vary. For practical purposes, the amount of sample and the size of the device may limit the number of arrays to between one and twenty, such as between two and ten, or between two and five. The fluid path 40 may comprises branched region 499 to facilitate the number of BAW arrays.

Each of the BAW arrays (361, 362, 363, 364, etc.) of the BAW sensor 30 may include a viscosity sensor 330 and one or more specific-binding sensor 313 as shown in FIG. 10B. Each sensor 330, 313 may include one or more BAW resonators. Each array (361, 362, 363, 364, etc.) may include an isolated environmental BAW reference 314, or a single isolated environmental BAW reference 314 may be shared among one or more arrays.

The number of resonators on the sensor 30 can also be divided into testing resonators and reference resonators in any suitable way. The sensing portion of the fluid flow path 40 may be configured so that the sample (or other fluid) in the fluid flow path 40 does not come into contact with the isolated environmental BAW reference 314.

As shown in FIG. 10A, the BAW sensing device 10 may include a first fluid port 50 and a first fluid channel 501 connecting the first fluid port 50 to the fluid flow path 40. The fluid flow path 40 may include a first mixing valve 502 at the connection of the first fluid channel 501. The BAW sensing device 10 may also include a second fluid port 60 and a second fluid channel 601 connecting the second fluid port 60 to the fluid flow path 40, as well as a second mixing valve 602 at the connection for the second fluid channel 601 and the fluid flow path 40. The section of the fluid flow path 40 extending between the first and second mixing valves 505, 605 may serve as a sample reservoir 411 having a volume V411.

The BAW sensing device 10 may include various features for interfacing with the reader 2. For example, the first and second fluid ports 50, 60 may interface with valves, pumps, or other fluidic interfaces for pneumatic or liquid-based fluid transfer systems on the reader. The BAW sensing device 10 may also include mechanical registrations to position the BAW sensing device within the reader 2, and one or more interfaces 801 for electrical current (e.g., direct current or alternating current) and power and digital communication signals, magnetic interfaces, thermal interfaces, and/or optical interfaces.

The BAW sensing device 10 may further include a waste reservoir 70. The waste reservoir 70 may be located at the distal end 42 of the fluid flow path 40. The waste reservoir 70 may be constructed to receive the sample and any fluids used to process the sample (e.g., agents and fluids injected through the first and second fluid ports 50, 60) after the sample and the fluids have progressed through the BAW sensor 30. The volume of the waste reservoir 70 is not particularly limited and can range from about 100 µL to about 2 mL. The waste reservoir 70 may also include a vent 72 that allows air or gases but not fluids to escape from the waste reservoir 70. The vent 72 may, for example, be covered by a hydrophobic membrane.

Figure 11:
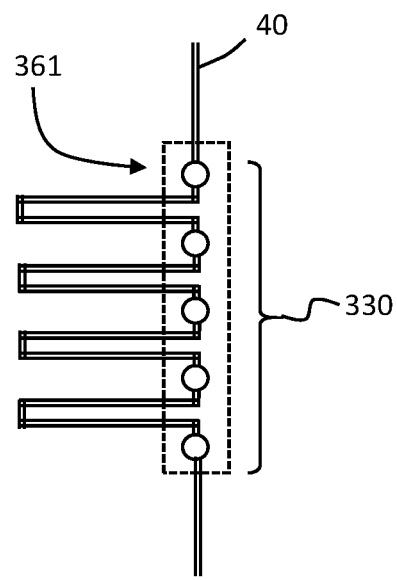
FIG. 11 is a schematic plan view of an embodiment of an array of resonators and flow path of a BAW sensing device.

Referring now to FIG. 11, an alternative flow path 40 through an array 361 of resonators that may serve as a viscosity sensor 330 is shown. The flow path 40 is extended between resonators rather that flowing in a straight line from one resonator to another. The extended flow path depicted in FIG. 11 may be advantageous to provide additional time for the sample flowing through the path 40 to reach the next resonator, which may be advantageous to detect changes in coagulation of the blood in the sample over time.

Figure 12:
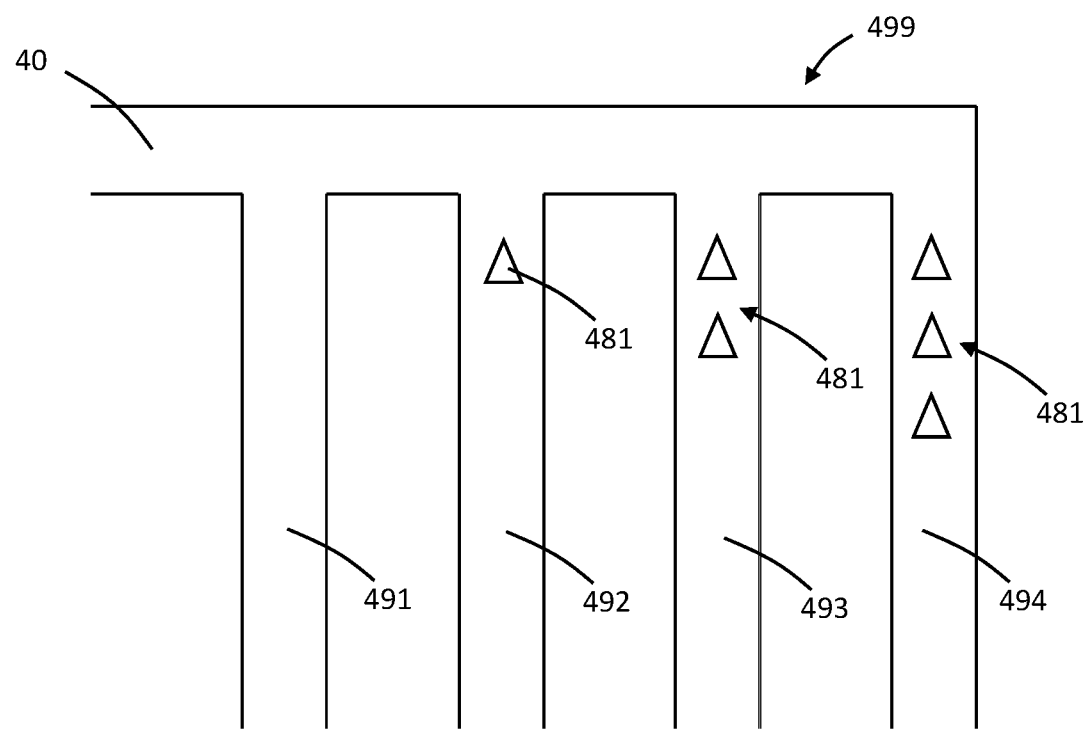
FIG. 12 is a schematic plan view of an embodiment of a branched portion of a flow path of a BAW sensing device.

Referring now to FIG. 12, an example of a branched region 499 of a flow path 40 that may deliver the sample to difference sensing arrays is shown. The first branched path 491 does not include an agitator. The second flow path 492 includes an agitator 481 for providing low levels of agitation to the sample as it flows through the second branched path 492. The third flow path 493 includes an agitator 481 for providing medium levels of agitation to the sample as it flows through the third branched path 493. The fourth flow path 494 includes an agitator 481 for providing high levels of agitation to the sample as it flows through the fourth branched path 494. Agitation of the sample may promote coagulation of the blood, and more vigorous agitation may promote faster coagulation. Accordingly, the branched region 499 or any other suitable region of a flow path 40 may adapted to evaluate characteristics of coagulation of the blood in the sample in response to agitation or differing levels of agitation, which may provide meaningful information regarding the blood in the sample.

It will be understood that the branched flow path 499 depicted in FIG. 12 is only one example of a branched region 499 that may be employed in a BAW sensing device and that other branched flow paths and agitation schemes are contemplated. It will be further understood that the agitation scheme depicted in FIG. 12 or any other suitable agitation scheme may be employed with any other aspects of flow paths described herein. For example, the flow path 40 through the array 361 shown in FIG. 11 may be placed downstream of the branched paths (491, 492, 493, 494) depicted in FIG. 12.

Any suitable agitation element 481 or combination of elements may be employed to agitate the sample. Agitation may be active or passive. Examples of active agitation include acoustic or ultrasonic, dielectrophoretic, electrokinetic time-pulse, pressure perturbation, electro-hydrodynamic, magnetic or thermal agitation. Examples of passive agitation include placement of one or more features or valves, such as a Venturi valve, in the flow path to cause turbulent flow. Preferably, the agitation is passive.

Figure 13:
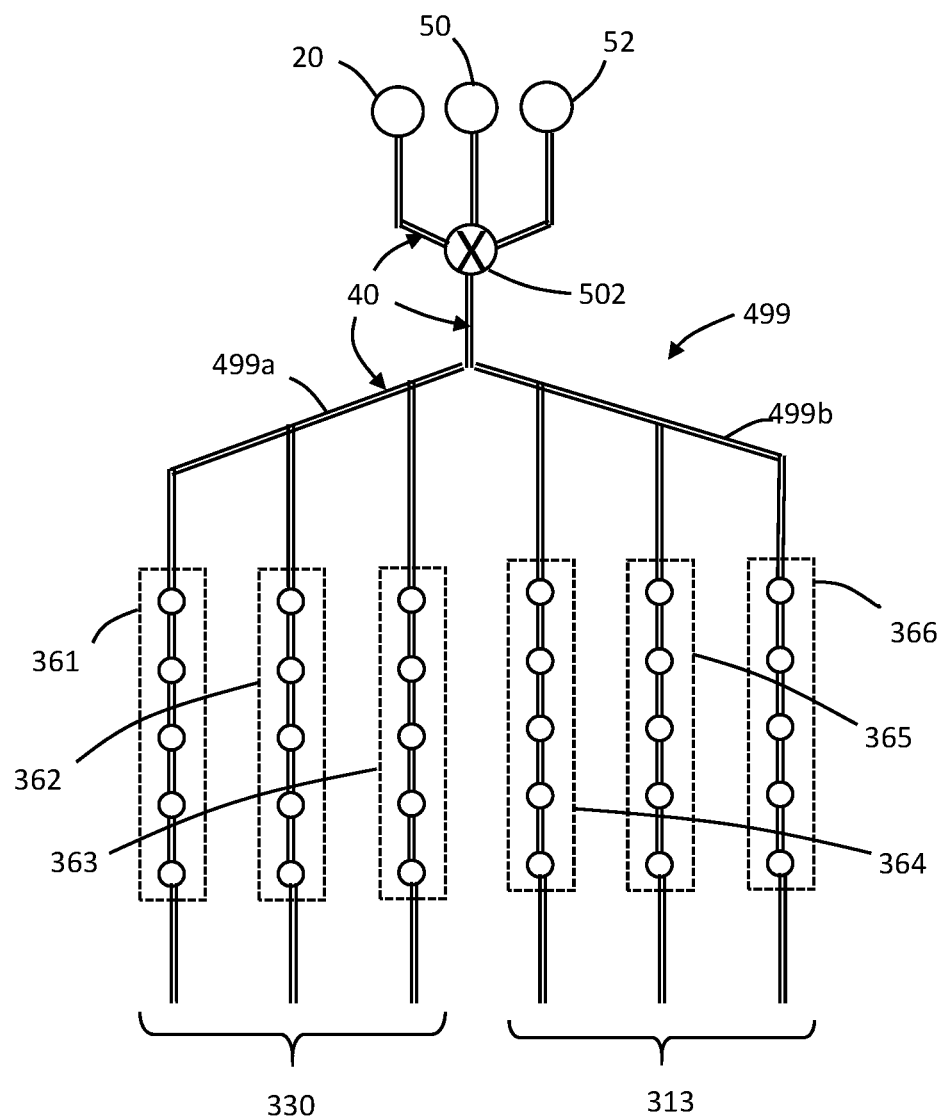
FIG. 13 is a schematic plan view of an embodiment of fluid handling components, a flow path, and arrays of resonators of a BAW sensing device.

Referring now to FIG. 13, another example of fluid flow and sensor arrays 361-366 that may be employed with devices, methods and systems described herein is shown. A flow path 40 extends from a sample port 20 to resonators of arrays 361-366, and may extend to a waste chamber. The flow path 40 includes a branched portion 499 that includes a first branched portion 499a and a second branched portion 499b that provide separate branches across resonators of arrays 361-366. The first branched portion 499a may be similar to the branched portion 499 depicted in FIG. 12 and may include one or more agitators. The first branched portion 499a causes the sample to flow across arrays 361, 362, 363 of resonators that together form a viscosity sensor 330. The second branched portion 499b causes the sample to flow across arrays 364, 365, 366 of resonators. One or more resonators in each array 364, 365, 366 may comprise a biomolecule on the sensing surface of the resonator, where the biomolecule is configured to specifically bind to one or more component or molecule of blood. One or more resonators in each array 364, 365, 366 may have no specific binding biomolecule, but may serve as a reference for non-specific binding that may occur at the surface. The arrays 364, 365, 366 together form a sensor 313 for detecting one or more blood species. Information regarding the presence or concentration of one or more blood species may be determined by species sensor portion 313 and may be combined with information from the viscosity sensor portion 330 to derive a wealth of knowledge regarding the coagulation status of blood in the sample.

A buffer or other suitable fluid may be introduced through fluid port 50 to force the sample through the flow path 40. In addition, one or more agents that may be introduced through a fluid port 50 or 52 to be mixed with the sample by mixer 502 upstream of the sensors to allow additional information to be obtained regarding the coagulation status of the blood in the sample.

Figure 14:
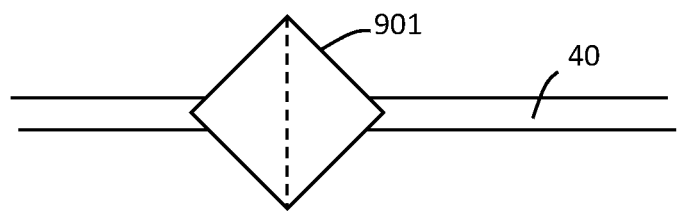
FIG. 14 is a schematic plan view of an embodiment of a portion of a flow path of a BAW sensing device having a filter.

Referring now to FIG. 14, the flow path 40 of any of the devices described herein or in any suitable device for carrying out the methods described herein may include one or more filter 901. The filter may be positioned at any suitable location in the flow path 40. The filter 901 may filter out coagulated portions of blood to avoid blockage of the flow path 40 and may allow non-coagulated portions, such as platelets, to pass for analysis by the sensors. Any suitable filter may be used. For example, a micropore ceramic or sintered metal filter may be used.

The BAW sensing device of the present disclosure utilize sensors with bulk acoustic wave (BAW) resonators. According to various embodiments, the cartridge contains a BAW array in a fluid flow path. BAW resonators generally include a piezoelectric crystal resonator that can be used to detect changes in material (e.g., changes in the mass of the material) deposited (e.g., bound) on the surface of the resonator or properties (e.g., viscosity) of fluid at the surface of the resonator. The BAW resonator may have biomolecules, such as antibodies or other proteins such as receptors, polynucleic acids, or the like, attached to its surface such that when the target analyte (e.g., molecule or component of blood) passes over the surface, it binds onto the biomolecule. The cartridge may be prepared with various select biomolecules based on the desired target analyte or analytes.

BAW devices typically involve transduction of an acoustic wave using electrodes arranged on opposing top and bottom surfaces of a piezoelectric material. In a BAW device, three wave modes may propagate, namely, one longitudinal mode (embodying longitudinal waves, also called compressional/extensional waves), and two shear modes (embodying shear waves, also called transverse waves), with longitudinal and shear modes respectively identifying vibrations where particle motion is parallel to or perpendicular to the direction of wave propagation. The longitudinal mode is characterized by compression and elongation in the direction of the propagation, whereas the shear modes consist of motion perpendicular to the direction of propagation with no local change of volume. Longitudinal and shear modes propagate at different velocities. In practice, these modes are not necessarily pure modes as the particle vibration, or polarization, is neither purely parallel nor purely perpendicular to the propagation direction. The propagation characteristics of the respective modes depend on the material properties and propagation direction respective to the crystal axis orientations. The ability to create shear displacements is beneficial for operation of acoustic wave devices with fluids (e.g., liquids) because shear waves do not impart significant energy into fluids. BAW devices include bulk acoustic resonators deposited on one or more reflective layers, such as Bragg mirror, and film bulk acoustic resonators having an air-gap.

The BAW sensor described herein may employ any suitable piezoelectric thin film. Certain piezoelectric thin films are capable of exciting both longitudinal and shear mode resonance, such as hexagonal crystal structure piezoelectric materials including (but not limited to) aluminum nitride (AlN) and zinc oxide (ZnO). To excite a wave including a shear mode using a piezoelectric material layer arranged between electrodes, a polarization axis in a piezoelectric thin film is generally non-perpendicular to (e.g., tilted relative to) the film plane. In sensing applications involving liquid media, the shear component of the resonator is preferably used. In such applications, piezoelectric material may be grown with a c-axis orientation distribution that is non-perpendicular relative to a face of an underlying substrate to enable a BAW resonator structure to exhibit a dominant shear response upon application of an alternating current signal across electrodes thereof. Conversely, a piezoelectric material grown with a c-axis orientation that is perpendicular relative to a face of an underlying substrate will exhibit a dominant longitudinal response upon application of an alternating current signal across electrodes thereof.

For purposes of detecting viscosity, the BAW sensor may be configured in a Thickness Shear Wave (TSW) oscillation mode. In this mode, conversion of radio frequency (RF) energy in the device may create a shear wave in the bulk of the device, perpendicular to the propagation of RF energy, where the maximum displacement of the shear wave is at the surface boundary. The device may be used as a viscosity sensor, since a fluid may be placed into contact with the sensor surface, thereby applying a mechanical load to the sensor acoustic motion.

When a viscous liquid is in contact with the sensor surface, loading occurs that can be described or modeled as an increase in the inductive behavior and a concomitant increase in the resistive behavior of the sensor. These loading conditions generally produce a decrease in the operating frequency of the sensor, which can be detected using appropriate electronic measurement devices. The higher the viscosity of the liquid, the greater the decrease in operating frequency. In addition, this viscous loading of the sensor results in a change in the resonate Q-value for the mode being used for sensing. This decrease of Q can also be used to gain further information regarding the fluidic properties of the blood.

Figure 15A:
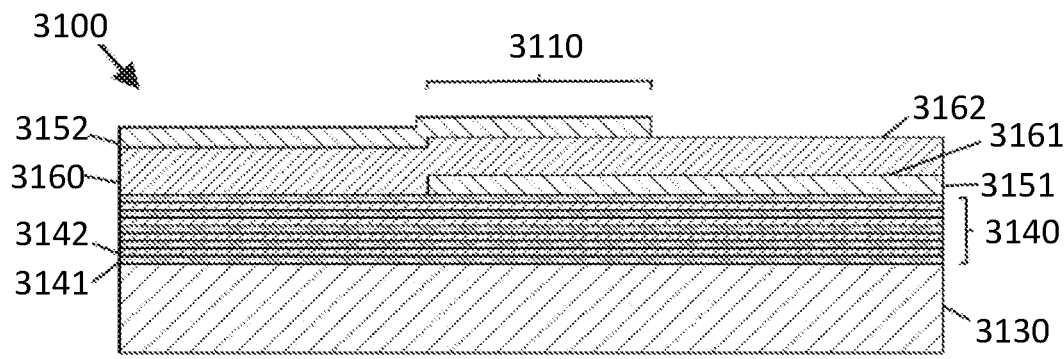
FIGS. 15A and 15B are schematic cross-sectional views of bulk acoustic wave resonators.

FIG. 15A is a schematic cross-sectional view of a portion of a bulk acoustic wave (BAW) Microelectromechanical system (MEMS) resonator structure 3100 useable with embodiments disclosed herein. The resonator structure 3100 includes a substrate 3130 (e.g., typically silicon or another semiconductor material), an acoustic reflector 3140 arranged over the substrate 3130, a piezoelectric material 3160, and bottom and top side electrodes 3151, 3152. The bottom side electrode 3151 is arranged along a portion of a lower surface 3161 of the piezoelectric material 3160 (between the acoustic reflector 3140 and the piezoelectric material 3160), and the top side electrode 3152 is arranged along a portion of an upper surface 3162 of the piezoelectric material 3160. An area in which the piezoelectric material 3160 is arranged between overlapping portions of the top side electrode 3152 and the bottom side electrode 3151 is considered an active region 3110 of the resonator device 3100 to which a biomolecule, if employed, is preferably applied. When the resonator structure 3100 is used to detect viscosity, a specific binding biomolecule is preferably not applied to the active region 3110. However, it may be desirable to apply a wetting agent, such as a surfactant, to the active region so that air pockets do not form when the sample or a preconditioning fluid flows across the active region, but rather uniform wetting occurs. In addition or alternatively, the active region 3110 of the resonator structure 3100 may be provided with a non-stick surface, such as a polytetrafluoroethylene (PTFE) coating, so that active region 3110 may be used more than once, such as to run of a sample and a sample mixed with an agent over the resonator structure 3100 at different times.

The acoustic reflector 3140 serves to reflect acoustic waves and therefore reduce or avoid their dissipation in the substrate 3130. In certain embodiments, the acoustic reflector 3140 includes alternating thin layers 3141, 3142 of materials (e.g., silicon oxicarbide [SiOC], silicon nitride [$Si_3N_4$], silicon dioxide [$SiO_2$], aluminum nitride [AlN], tungsten [W], and molybdenum [Mo]) having different acoustic impedance values, optionally embodied in a quarter-wave Bragg mirror, deposited over the substrate 3130. In certain embodiments, other types of acoustic reflectors may be used. Steps for forming the resonator device 30 may include depositing the acoustic reflector 3140 over the substrate 3130, followed by deposition of the bottom side electrode 3151, followed by growth (e.g., via sputtering or other appropriate methods) of the piezoelectric material 3160, followed by deposition of the top side electrode 3152.

In certain embodiments, the piezoelectric material 3160 comprises a hexagonal crystal structure piezoelectric material (e.g., aluminum nitride or zinc oxide) that includes a c-axis having an orientation distribution that is predominantly non-parallel (and may also be non-perpendicular to) to normal of a face of the substrate 3130. Under appropriate conditions, presence of a c-axis having an orientation distribution that is predominantly non-parallel to normal of a face of a substrate enables a BAW resonator structure to be configured to exhibit a dominant shear response upon application of an alternating current signal across a distal electrode and a proximal electrode thereof (e.g., as may be desirable in the context of a BAW resonator structure providing sensing utility). Methods for forming hexagonal crystal structure piezoelectric materials including a c-axis having an orientation distribution that is predominantly non-parallel to normal of a face of a substrate are disclosed in U.S. patent application Ser. No. 15/293,063 filed on Oct. 13, 2016. Additional methods for forming piezoelectric materials having an inclined c-axis orientation are disclosed in U.S. Pat. No. 4,640,756 issued on Feb. 3, 1987.

The bulk acoustic wave MEMS resonator structure 3100 shown in FIG. 15A lacks any layers (e.g., including functionalization material) overlying the active region 3110 that may permit the resonator device 3100 to be used as a biochemical sensor. If desired, at least portions of the resonator device 3100 shown in FIG. 15A (e.g., including the active region 3110) may be overlaid with various layers, such as one or more of: a hermeticity layer, an interface layer, a self-assembled monolayer (SAM), and/or a functionalization material layer (which may include specific binding material or non-specific binding material).

Figure 15B:
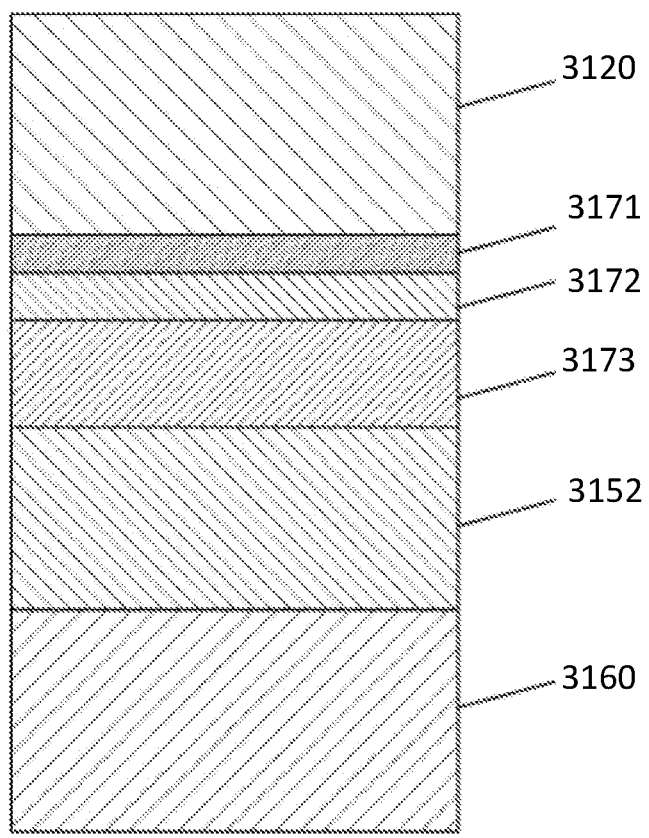

FIG. 15B is a schematic cross-sectional view of an upper portion of a BAW resonator device including a piezoelectric material 3160 and a top side electrode 3152 overlaid with a hermeticity layer 3171, an interface layer 3172, a self-assembled monolayer (SAM) 3173, and a layer 3120 comprising a biomolecule. In certain embodiments, one or more blocking materials (not shown) may be applied during fabrication, such as over portions of an interface layer to prevent localized attachment of one or more subsequently deposited layers, or (if applied over selected regions of a SAM or a functionalization material) to prevent analyte capture in regions not overlying an active region of the BAW resonator device. As an alternative to a biomolecule, layer 3120 may include a wetting agent or non-stick agent as described above.

In certain embodiments incorporating electrode materials subject to corrosion, a hermeticity layer may be applied between a top side electrode and an interface layer. If provided, a hermeticity layer preferably includes a dielectric material with a low water vapor transmission rate (e.g., no greater than 0.1 g/m$^2$/day). Following deposition of a hermeticity layer and an interface layer, a SAM may be formed over the interface layer, with the SAM including an organosilane material in certain embodiments. The hermeticity layer protects a reactive electrode material (e.g., aluminum or aluminum alloy) from attack in corrosive liquid environments, and the interface layer facilitates proper chemical binding of the SAM.

Following deposition of an interface layer (optionally arranged over an underlying hermeticity layer), a SAM is preferably formed over the interface layer. SAMs are typically formed by exposure of a solid surface to amphiphilic molecules with chemical groups that exhibit strong affinities for the solid surface. When an interface layer comprising a hydroxylated oxide surface is used, then organosilane SAMs are particularly preferred for attachment to the hydroxylated oxide surface. Organosilane SAMs promote surface bonding through silicon-oxygen (Si—O) bonds.

When an electrode and/or interface layer comprising gold or another noble metal is used, then thiol-based (e.g., alkanethiol-based) SAMs may be used. Alkanethiols are molecules with an alkyl chain as the back bone, a tail group, and an S—H head group. Thiols may be used on noble metal interface layers due to the strong affinity of sulfur for these metals.

Following formation of a SAM, the SAM may be biologically functionalized, such as by receiving at least one specific binding material. In certain embodiments, specific binding materials may be applied on or over a SAM using a microarray spotting needle or other suitable methods. In certain embodiments, an interface layer may be patterned (e.g., using photolithography for defining the interface layer) with a high dimensional tolerance over only a portion of a resonator structure (which includes a substrate), a SAM may be applied over the interface layer, and a subsequently applied specific binding material may be attached only to the SAM. In certain embodiments, patterning of an interface layer may provide a higher dimensional tolerance for positioning of the specific binding material than could be attained by microarray spotting alone. Examples of specific binding materials include, but are not limited to, antibodies, receptors, ligands, oligopeptides, DNA or RNA strands, and the like. A specific binding material is preferably configured to receive a predefined target species (e.g., molecule, protein, DNA, virus, bacteria, etc.). A functionalization material including specific binding material may include a thickness in a range of from about 5 nm to about 1000 nm, or from about 5 nm to about 500 nm. In certain embodiments, an array of different specific binding materials may be provided over different active areas of a multi-resonator structure (i.e., one or more resonator structures including multiple active regions), optionally in combination with one or more active areas that are devoid of specific binding materials to serve as comparison (or "reference") regions. In certain embodiments, a functionalization material (e.g., chemical functionalization material) may provide non-specific binding utility.

Certain embodiments of the present disclosure are directed to a BAW sensing device including multiple BAW resonators as disclosed herein and including a fluidic passage (e.g., a channel, a chamber, or the like) arranged to conduct a liquid to contact at least one functionalization (e.g., specific binding) material arranged over at least one active sensing surface of the resonators. Such a device may be microfluidic in scale, and comprise at least one microfluidic passage (e.g., having at least one dimension, such as height and/or width, of no greater than about 1000 microns, no greater than about 500 microns, or no greater than about 250 microns, or no greater than about 100 microns).

The BAW sensing device, other external components such as a reader, or a combination thereof comprises appropriate electronics to drive the resonators into an oscillating motion and to measure a change in a characteristic of the oscillating motion of the resonator due to, for example, fluid properties (such as viscosity) of a sample or binding of molecules from a sample to the surface of the sensor. Any suitable electronics may be used to accomplish these functions. In some embodiments, a lever oscillator, and emitter-coupled oscillator, and emitter-couple oscillator coupled with gain and phase control, a Butler oscillator, or oscillation electronics described in, for example, U.S. Pat. No. 8,409,875 or PCT Patent Application Publication No. WO 2014/143680 may be employed.

A BAW sensing device may comprise temperature control (resistive heating elements or cooling elements) at the sensing surface or at any other suitable location to maintain or change temperature to enhance sensitivity and reproducibility of the results or to gain further insight into the fluid characteristics of the sample containing the blood. Temperature control may be accomplished as described in, for example, U.S. Provisional Patent Application Nos. 62/368,261 (filed 29 Jul. 2016) or 62/370,788 (filed on 4 Aug. 2016), each of which provisional patent applications are hereby incorporated herein by reference in their respective entireties to the extent that they do not conflict with the disclosure presented herein.

Electronic components may be provided in any suitable form and may, for example, include a controller or a memory and a controller. The controller may include one or more of an Application Specific Integrated Circuit (ASIC) state machine, a digital signal processor, a gate array, a resonance circuit, a microprocessor, or equivalent discrete or integrated logic circuitry. Electronics may include memory that contains instructions that cause one or more components of the circuitry to carry out a function or aspect of the control electronics. Functions attributable to electronics in this disclosure may be embodied as one or more of software, firmware, and hardware.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open-ended sense, and generally mean "including, but not limited to." It will be understood that "consisting essentially of," "consisting of," and the like are subsumed in "comprising" and the like. As used herein, "consisting essentially of," as it relates to a composition, product, method or the like, means that the components of the composition, product, method or the like are limited to the enumerated components and any other components that do not materially affect the basic and novel characteristic(s) of the composition, product, method or the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" a particular value, that value is included within the range.

Any direction referred to herein, such as "top," "bottom," "left," "right," "upper," "lower," and other directions and orientations are described herein for clarity in reference to the figures and are not to be limiting of an actual device or system or use of the device or system. Devices or systems as described herein may be used in a number of directions and orientations.

The invention claimed is:

1. A method of measuring coagulation properties of blood in a sample over a period of time, the method comprising:
   driving a first bulk acoustic wave (BAW) resonator, a second bulk acoustic wave (BAW) resonator, and a third bulk acoustic wave (BAW) resonator, each comprising a sensing surface, into an oscillating motion;
   flowing the sample through a flow path comprising the first, second, and third bulk acoustic wave (BAW) resonators, wherein the flow path comprises two or more branches arranged in parallel with one another, wherein at least two of the two or more branches each include at least one BAW resonator; and
   detecting a resonance characteristic of each oscillating BAW resonator while the sample is in contact with the sensing surface, wherein the resonance characteristic of the first BAW resonator is detected at a first time point, and the second BAW resonator detects a resonance characteristic at a second time point in sequence after the first time point.

2. The method of claim 1, wherein the first BAW resonator is adapted to measure a viscosity of the sample;
   wherein the second BAW resonator (i) is adapted to measure the viscosity of the sample or (ii) comprises a biomolecule on the sensing surface of the second BAW resonator that specifically binds to a component or molecule of the blood in the sample; and
   wherein the third BAW resonator (i) is adapted to measure the viscosity of the sample or (ii) comprises a biomolecule on the sensing surface of the third BAW resonator that specifically binds to a component or molecule of the blood in the sample.

3. The method of 2, further comprising:
   converting the resonance characteristic of the first BAW resonator into a value indicating the viscosity of the sample;
   converting the resonance characteristic of the second BAW resonator (i) into a value indicating the viscosity of the sample or (ii) into a concentration of the component or molecule of the blood in the sample;
   detecting a resonance characteristic at the third BAW resonator, and converting the resonance characteristic of the third BAW resonator (i) into a value indicating the viscosity of the sample or (ii) into a concentration of the component or molecule of the blood in the sample; and
   using the value indicating the viscosity of the sample and the concentration of the component or molecule of the blood in the sample to measure the coagulation properties of the blood in the sample.

4. The method of claim 3, further comprising mixing the sample with a coagulation-modifying agent prior to flowing the sample across the sensing surface of the first BAW resonator, the second BAW resonator, the third BAW resonator, or any combination thereof.

5. The method of claim 4, wherein the coagulation-modifying agent comprises a coagulation inhibitor.

6. The method of claim 5, further comprising using the viscosity of the sample from the first BAW resonator, the second BAW resonator, or any combination thereof, to determine an appropriate dosage of the coagulation inhibitor to provide to a patient for whom coagulation inhibitor therapy is indicated.

7. The method of claim 4, further comprising mixing the sample with a plurality of coagulation-modifying agents or combinations thereof and determining the effect of the coagulation-modifying agents or combinations thereof on the coagulation properties of the blood in the sample.

8. The method of claim 4, wherein the coagulation-modifying agent comprises a platelet activator.

9. The method of claim 1, wherein the first, second, or third BAW resonators, or any combination thereof, are arranged in series.

10. The method of claim 1, wherein the first, second, and third BAW resonators, or any combination thereof, are arranged in an array.

11. The method of claim 1, further comprising detecting a resonance characteristic of an isolated environmental BAW reference resonator that does not come in contact with the sample.

12. The method of claim 2, further comprising comparing the viscosity measured from the first BAW resonator with the viscosity measured from the second BAW resonator when the second BAW resonator is adapted to measure the viscosity of the sample, the third BAW resonator when the third BAW resonator is adapted to measure the viscosity of the sample, or both.

13. The method of claim 1, further comprising flowing the sample across the sensing surface of the first BAW resonator before flowing the sample across the sensing surface of the third BAW resonator.

14. The method of claim 13, further comprising flowing the sample across the sensing surface of the second BAW resonator before flowing the sample across the sensing surface of the third BAW resonator.

15. The method of claim 1, further comprising agitating at least a portion of the sample.

16. The method of claim 15, wherein agitating at least a portion of the sample comprises active agitation or passive agitation.

17. The method of claim 16, wherein agitating at least a portion of the sample comprises passive agitation comprising placement of one or more features or valves in the flow path to cause turbulent flow.

18. A method of measuring coagulation properties of blood in a sample, the method comprising:
   driving a first bulk acoustic wave (BAW) resonator, a second bulk acoustic wave (BAW) resonator, and a third bulk acoustic wave (BAW) resonator, each comprising a sensing surface, into an oscillating motion;
   flowing the sample through a flow path comprising the first, second, and third bulk acoustic wave (BAW) resonators;
   detecting a resonance characteristic of each oscillating BAW resonator while the sample is in contact with the sensing surface; and
   agitating at least a portion of the sample, wherein:
   a first portion of the sample is not agitated before flowing the first portion of the sample across the sensing surface of the first BAW resonator;
   a second portion of the sample is agitated before flowing the second portion of the sample across the sensing surface of the second BAW resonator; and
   a third portion of the sample is agitated before flowing the third portion of the sample across the sensing surface of the third BAW resonator.

19. The method of claim 18, wherein the second portion of the sample is agitated to a different degree than the third portion of the sample.

20. A method of measuring coagulation properties of blood in a sample, the method comprising:
   driving a first bulk acoustic wave (BAW) resonator, a second bulk acoustic wave (BAW) resonator, and a third bulk acoustic wave (BAW) resonator, each comprising a sensing surface, into an oscillating motion;
   flowing the sample through a flow path comprising the first, second, and third bulk acoustic wave (BAW) resonators, wherein the flow path comprises two or more branches arranged in parallel with one another, wherein at least two of the two or more branches each include at least one BAW resonator; and
   detecting a resonance characteristic of each oscillating BAW resonator while the sample is in contact with the sensing surface.

* * * * *

UNITED STATES PATENT AND TRADEMARK OFFICE
CERTIFICATE OF CORRECTION

| | | |
|---|---|---|
| PATENT NO. | : 12,360,125 B2 | Page 1 of 1 |
| APPLICATION NO. | : 16/319412 | |
| DATED | : July 15, 2025 | |
| INVENTOR(S) | : Florian Bell et al. | |

It is certified that error appears in the above-identified patent and that said Letters Patent is hereby corrected as shown below:

In the Specification

Column 1, Line 5, please delete "$" and insert -- § --.

Signed and Sealed this
Twelfth Day of August, 2025

Coke Morgan Stewart
*Acting Director of the United States Patent and Trademark Office*